US008114422B2

(12) United States Patent
Fujii et al.

(10) Patent No.: US 8,114,422 B2
(45) Date of Patent: Feb. 14, 2012

(54) METHODS AND COMPOSITIONS FOR REDUCING SKIN DAMAGE

(75) Inventors: Seishiro Fujii, Kanagawa-Ken (JP); Gian Paolo Dotto, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1638 days.

(21) Appl. No.: 11/497,870

(22) Filed: Jul. 31, 2006

(65) Prior Publication Data

US 2007/0104746 A1 May 10, 2007

Related U.S. Application Data

(60) Provisional application No. 60/703,982, filed on Jul. 29, 2005.

(51) Int. Cl.
*A61K 8/02* (2006.01)
*A61K 8/18* (2006.01)
(52) U.S. Cl. ............ 424/401; 424/59; 424/407; 424/60; 514/520; 514/150; 514/249
(58) Field of Classification Search .................. 424/401, 424/59, 407; 514/12, 150, 249, 520
See application file for complete search history.

(56) References Cited

U.S. PATENT DOCUMENTS

| 5,120,546 A | * | 6/1992 | Hansen et al. ................. 424/449 |
| 5,554,359 A | * | 9/1996 | Fuller ............................... 424/59 |
| 5,955,502 A | * | 9/1999 | Hansen et al. ................. 514/558 |
| 5,958,458 A | * | 9/1999 | Norling et al. ................ 424/490 |

| 2004/0057942 A1 | * | 3/2004 | Vacanti et al. .............. 424/93.21 |
| 2005/0136537 A1 |   | 6/2005 | Sinclair et al. |
| 2006/0128619 A1 |   | 6/2006 | Champion et al. |

FOREIGN PATENT DOCUMENTS

WO WO 2005/052187 6/2005

OTHER PUBLICATIONS

Fewell (Effects of sun on the skin, retrieved from the internet on Feb. 22, 2011, year 2004; URL: http://web.archive.org/web/20040805044713/dermatology.about.com/cs/beauty/a/suneffect.htm).*
Ayyanan et al., "Increased Wnt signaling triggers oncogenic conversion of human breast epithelial cells by a Notch-dependent mechanism," Proc. Natl. Acad. Sci. USA, 103:3799-3804 (2006).
Devgan et al., "p21$^{WAF1/Cip1}$ is a negative transcriptional regulator of *Wnt4* expression downstream of Notch1 activation," Genes Dev., 19:1485-95 (2005).
Dotto, "Crosstalk of Notch with p53 and p63 in cancer growth control," Nat. Rev. Cancer, 9:587-595 (2009).
Dotto, "Notch tumor suppressor function," Oncogene, 27:5115-23 (2008).
Grossi et al., "Negative control of keratinocyte differentiation by Rho/CRIK signaling coupled with up-regulation of KyoT1/2 (FHL1) expression," Proc. Natl. Acad. Sci. USA, 102:11313-18 (2005).

(Continued)

*Primary Examiner* — Jeffrey S. Lundgren
*Assistant Examiner* — Savitha Rao
(74) *Attorney, Agent, or Firm* — Fish & Richardson P.C.

(57) ABSTRACT

The Notch signal transduction pathway has been identified as a target for screening and treatment methods for the prevention and/or reduction of short- and long-term UVB-induced skin damage, e.g., the prevention and/or reduction of UVB-induced wrinkles. The invention thus features screening and treatment methods for prevention or reduction of UVB-induced sin damage, and related compositions, e.g., cosmetic compositions.

21 Claims, 3 Drawing Sheets

OTHER PUBLICATIONS

Huang et al., "Investigation of ouabain-induced anticancer effect in human androgen-independent prostate cancer PC-3 cells," Biochem. Pharmacol., 67:727-733 (2004).

Kolev et al., "EGFR signalling as a negative regulator of Notch1 gene transcription and function in proliferating keratinocytes and cancer," Nat. Cell Biol., 10:902-911 (2008).

Lefort and Dotto, "Notch signaling in the integrated control of keratinocyte growth/differentiation and tumor suppression," Semin. Cancer Biol., 14:374-378 (2004).

Lefort et al., "Notch1 is a p53 target gene involved in human keratinocyte tumor suppression through negative regulation of ROCK1/2 and MRCKalpha kinases," Genes Dev., 21:562-577 (2007).

Mammucari et al., "Integration of Notch 1 and calcineurin/NFAT signaling pathways in keratinocyte growth and differentiation control," Dev. Cell, 8:665-676 (2005).

Mandinova et al., "The FoxO3a gene is a key negative target of canonical Notch signalling in the keratinocyte UVB response," EMBO J., 27:1243-54 (2008).

Nguyen et al., "Cross-regulation between Notch and p63 in keratinocyte commitment to differentiation," Genes Dev., 20:1028-42 (2006).

Xu et al., "Cytochalasin D from *Hypocrella bambusae*," J. Asian Nat. Prod. Res., 3:151-155 (2001).

Artavanis-Tsakonas et al., "Notch Signaling: Cell Fate Control and Signal Integration in Development", Science 284:770-776, 1999.

Bennett et al., "SP600125, an Anthrapyrazolone Inhibitor of Jun N-Terminal Kinase", PNAS 98:13681-13686, 2001.

Bryckaert et al., "Inhibition of Platelet-Derived Growth Factor-Induced Mitogenesis and Tyrosine Kinase Activity in Cultured Bone Marrow Fibroblasts by Tyrphostins", Experimental Cell Research 199:255-261, 1992.

Collins et al., "Inositol 1,4,5-Trisphosphate-Induced $Ca^{2+}$ Release is Inhibited by Mitochondrial Depolarization", Biochem. J. 347:593-600, 2000.

Cooper, "Effects of Cytochalasin and Phalloidin on Actin", J. of Cell Biology 105:1473-1478, 1987.

Ellisen et al., "TAN-1, the Human Homolog of the Drosophila Notch Gene, Is Broken by Chromosomal Translocations in T Lymphoblastic Neoplasms", Cell 66:649-661, 1991.

Flanagan et al., "Cytochalasins Block Actin Filament Elongation by Binding to High Affinity Sites Associated with F-actin", J. of Biological Chemistry 255:835-838, 1980.

Furlong et al., "Intracellular Acidification Induces Apoptosis by Stimulating ICE-like Protease", J. Cell Science 110:653-661, 1997.

Gautier et al., "A Moderate but Not Total Decrease of Mitochondrial Membrane Potential Triggers Apoptosis in Neuron-like Cells", Membrane and Cellular Biophysics and Biochemistry 11:2953-2956, 2000.

GenBank Accession No. NM 017617, Jul. 13, 2005.

Goddette et al., "Actin Polymerization", J. of Biological Chemistry 261:15974-15980, 1986.

Han et al., "c-Jun N-terminal Kinase is Required for Metalloproteinase Expression and Joint Destruction in Inflammatory Arthritis", J. of Clinical Investigation 108:73-81, 2001.

Hayward et al., "Notch and Wnt Signaling: Mimicry and Manipulation by Gamma Herpesviruses", Science STKE, 2006:re4, 2006.

Hayward, "Viral Interactions with the Notch Pathway", Seminars in Cancer Biology 14:387-396, 2004.

Itoh et al., "Synergy and Antagonism between Notch and BMP Receptor Signaling Pathways in Endothelial Cells", The EMBO Journal 23:541-551, 2004.

Jarriault et al., "Signalling Downstream of Activated Mammalian Notch", Nature 377:355-358, 1995.

Kau et al., "Nuclear Transport and Cancer: From Mechanism to Intervention", Nature Reviews Cancer 4:106-117, 2004.

Kau et al., "Nuclear Transport as a Target for Cell Growth", Drug Discovery Today 8:78-85, 2003.

Keij et al., "Staining of Mitochondrial Membranes with 10-Nonyl Acridine Orange MitoFluor Green, and MitoTracker Green Is Affected by Mitochondrial Membrane Potential Altering Drugs", Cytometry 39:203-210, 2000.

Kovalenko et al., "Phosphorylation Site-Specific Inhibition of Platelet-Derived Growth Factor β-Receptor Autophosphorylation by the Receptor Blocking Tyrphostin AG1296", Biochemistry 36:6260-6269, 1997.

Krystal et al., "Induction of Apoptosis and Inhibition of Small Cell Lung Cancer Growth by the Quinoxaline Tyrphostins", Cancer Research 57:2203-2208, 1997.

Laux et al., "Identification and Characterization of an Epstein-Barr Virus Nuclear Antigen 2-Responsive cis Element in the Bidirectional Promoter Region of Latent Membrane Protein and Terminal Protein 2 Genes", J. of Virology 68:6947-6958, 1994.

Laux et al., "The Spi-1/PU.1 and Spi-B ets Family Transcription Factors and the Recombination Signal Binding Protein $RBP-J_k$ Interact with an Epstein-Barr Virus Nuclear Antigen 2 Responsive CIS-Element", The EMBO Journal 13:5624-5632, 1994.

Levitzki et al., "Tyrphostins as Molecular Tools and Potential Antiproliferative Drugs", Trends Pharmacol. Sci. 12:171-174, 1991.

Lichtstein et al., "Digitalis and Digitalislike Compounds Down-Regulate Gene Expression of the Intracellular Signaling Protein 14-3-3 in Rat Lens", Hypertens. Res. 23:S51-S53, 2000.

Liu et al., "Regulation of Notch1 and Dll4 by Vascular Endothelial Growth Factor in Arterial Endothelial Cells: Implications for Modulating Arteriogenesis and Angiogenesis", Molecular and Cellular Biology 23:14-25, 2003.

Maier et al., "Comparative Analysis of the Human and Mouse Hey1 Promoter: Hey Genes are New Notch Target Genes", Biochemical and Biophysical Research Communications 275:652-660, 2000.

McDonough et al., "The Cardiac Sodium Pump: Structure and Function", Basic Res. Cardiol. 97:I/19-I/24, 2002.

Mitchison, "Small-Molecule Screening and Profiling by Using Automated Microscopy", ChemBioChem 6:33-39, 2005.

Nicolas et al., "Notch1 Functions as a Tumor Suppressor in Mouse Skin", Nature Genetics 33:416-421, 2003.

Okuyama et al., "A Dynamic Model of Keratinocyte Stem Cell Renewal and Differentiation: Role of the $p21^{WAF1/Cip1}$ and Notch1 Signaling Pathways", J. Investig. Dermatol. Symp. Proc. 9:248-252, 2004.

Okuyama et al., "High Commitment of Embryonic Keratinocytes to Terminal Differentiation through a Notch1-caspase 3 Regulatory Mechanism", Developmental Cell 6:551-562, 2004.

Qi et al., "Notch1 Signaling Inhibits Growth of Human Hepatocellular Carcinoma Through Induction of Cell Cycle Arrest and Apoptosis", Cancer Research 63:8323-8329, 2003.

Rangarajan et al., "Notch Signaling is a Direct Determinant of Keratinocyte Growth Arrest and Entry into Differentiation", The EMBO Journal 20:3427-2436, 2001.

Schliwa, "Action of Cytochalasin D on Cytoskeletal Networks", The Journal of Cell Biology 92:79-91, 1982.

Schoner, "Endogenous Cardiac Glycosides, a New Class of Steroid Hormones", Eur. J. Biochem. 269:2440-2448, 2002.

Strutz et al., "TGF-β1 Induces Proliferation in Human Renal Fibroblasts Via Induction of Basic Fibroblast Growth Factor (FGF-2)", Kidney International 59:579-592, 2001.

Talora et al., "Specific Down-Modulation of Notch1 Signaling in Cervical Cancer Cells is Required for Sustained HPV-E6/E7 Expression and Late Steps of Malignant Transformation", Genes & Development 16:2252-2263, 2002.

Thélu et al., "Notch signalling is linked to epidermal cell differentiation level in basal cell carcinoma, psoriasis and wound healing," MBC Dermatol. 2:7, 2002.

Veldhuis et al., "Neuroprotection by the Endogenous Cannabinoid Anandamide and Arvanil against In Vivo Excitotoxicity in the Rat: Role of Vanilloid Receptors and Lipoxygenases", The Journal of Neuroscience 23:4127-4133, 2003.

Verceisi et al., "Thapsigargin Causes $Ca^{2+}$ Release and Collapse of the Membrane Potential of *Trypanosoma brucei* Mitochondria in Situ and of Isolated Rat Liver Mitochondria", The Journal of Biological Chemistry 268:8564-8568, 1993.

Weng et al., "Growth Suppression of Pre-T Acute Lymphoblastic Leukemia Cells by Inhibition of Notch Signaling", Molecular and Cellular Biology 23:655-664, 2003.

* cited by examiner

SEQUENCE LISTING

<160> NUMBER OF SEQ ID NOS: 2

<210> SEQ ID NO 1
<211> LENGTH: 6
<212> TYPE: DNA
<213> ORGANISM: Artificial Sequence -continued

```
<220> FEATURE:
<223> OTHER INFORMATION: conserved motif for RBP JR/CBF-1 binding

<400> SEQUENCE: 1 ggcgcc                                                                   6

<210> SEQ ID NO 2
<211> LENGTH: 7
<212> TYPE: DNA
<213> ORGANISM: Artificial Sequence
<220> FEATURE:
<223> OTHER INFORMATION: conserved motif for RBP JR/CBF-1 binding

<400> SEQUENCE: 2 gtgggaa                                                                  7
```

METHODS AND COMPOSITIONS FOR REDUCING SKIN DAMAGE

CROSS-REFERENCE TO RELATED APPLICATIONS

This application claims priority to U.S. Application Ser. No. 60/703,982, filed on Jul. 29, 2005, which is incorporated herein by reference in its entirety.

FEDERALLY SPONSORED RESEARCH OR DEVELOPMENT

The U.S. Government may have certain rights in this invention pursuant to Grant No. AR39190 awarded by the National Institute of Arthritis and Musculoskeletal and Skin Diseases.

BACKGROUND

The Notch receptors are cysteine-rich transmembrane polypeptides that are thought to mediate cell fate determination by acting as "gate keepers" that interpret environmental signals received by the cell. Depending on cell type and environmental context, activation of Notch may promote proliferation, differentiation, or even death. Activation of Notch cell-bound ligands (Delta and/or Jagged family members) results in the proteolytic cleavage of the intracellular domain of Notch (NICD) and its translocation to the cell nucleus, where it is recruited to target genes via interaction with RBP-Jκ, a DNA-binding component of the Notch pathway.

SUMMARY

The invention is based, in part, on the discovery that the Notch signal transduction pathway is important for the maintenance and/or appearance of skin. In one embodiment, the inventors have found that the Notch signal transduction pathway is important in the reduction, treatment, and/or prevention of skin damage, e.g., ultraviolet B (UVB)-induced skin damage and wrinkles. Therefore, the inventors have identified the Notch signal transduction pathway as a target for screening and therapeutic methods for the prevention and/or reduction of acute and/or chronic photodamage, e.g., UVB-induced skin damage (e.g., the prevention and/or reduction of wrinkles). The invention thus features screening and treatment methods for reduction, treatment, and/or prevention of UVB-induced skin damage, e.g., wrinkles, and related compositions, e.g., cosmetic compositions.

Accordingly, in one aspect, the invention features a method of screening for an agent that prevents and/or reduces UVB-induced skin damage, e.g., wrinkles. The method includes identifying an agent that increases or induces the expression, activity, or levels of a component of the Notch signal transduction pathway, e.g., a Notch protein (e.g., Notch1), a Delta protein, a Jagged protein, or RBP-Jκ, typically Notch1.

The method can also include associating increased expression, activity, or levels of a component of the Notch signal transduction pathway with the agent's ability to prevent or reduce wrinkles, e.g., identifying the identified agent as a wrinkle protection or reduction agent (e.g., providing print material or a computer readable medium, e.g., informational, marketing, or instructional print material or computer readable medium, related to the identified agent or its use). Associating means identifying a test agent that increases expression, activity or levels of a component of the Notch signal transduction pathway (and preferably increases Notch expression, levels or activity) as an agent capable of preventing, reducing or treating wrinkles. The associating step can include, e.g., generating or providing a record, e.g., a print or computer readable record, such as a laboratory record or dataset or an email, identifying a test agent that increases expression, activity or levels of a component of the Notch signal transduction pathway (and preferably increases Notch expression, levels or activity) as an agent capable of preventing, reducing or treating wrinkles. The record can include other information, such as a specific test agent identifier, a date, an operator of the method, or information about the source, structure, method of purification, or biological activity of the test agent. The record or information derived from the record can be used, e.g., to identify the test agent as a compound or candidate agent (e.g., a lead compound) for pharmaceutical or therapeutic use. The identified agent can be identified as an agent or a potential agent for treatment or reduction of wrinkles. Agents, e.g., compounds, identified by this method can be used, e.g., in the treatment (or development of treatments, e.g., cosmetic treatments) for wrinkles.

In one embodiment, the method includes evaluating, e.g., measuring, the effect of the agent on skin, e.g., evaluating a parameter correlated with wrinkles, e.g., the presence, extent, or type of wrinkles; and selecting an agent from the screen, e.g., an agent that prevents or reduces damage to the skin, e.g., prevents or reduces wrinkles in the skin. Preferably, evaluating the effect of the agent on skin includes administering the agent, e.g., topically, to a tissue or subject and comparing a parameter correlated with wrinkles, e.g., the presence, extent, or type of wrinkles in the tissue or subject, optionally with a reference value, e.g., a control or baseline value, e.g., a value for the same parameter in a tissue or subject that has been treated differently, e.g., has not been administered the agent or has been administered a placebo. The effect of the agent on skin can be evaluated in the absence or presence of a source of skin damage, e.g., an agent or treatment that induces wrinkle formation, e.g., UVB radiation. In some embodiments, the evaluation includes entering a value for the evaluation, e.g., a value for the presence, extent, or type of wrinkles into a database or other record.

In one embodiment, agent is evaluated for the ability to prevent or reduce UVB-induced wrinkles.

In another embodiment, the subject is an experimental animal, e.g., a wild-type or transgenic experimental animal, e.g., a rodent, e.g., a rat, mouse or guinea pig. The subject can also be a human. In a further embodiment, the evaluating step comprises administering the agent to the skin of the subject, e.g., topically.

In one embodiment, an agent that increases or induces the expression, activity or level of Notch is identified.

In another embodiment, the identifying step includes: (a) providing a cell, tissue or non-human animal harboring an exogenous nucleic acid that includes a regulatory region (e.g., a promoter or enhancer) of a component of the Notch signal transduction pathway operably linked to a nucleotide sequence encoding a reporter polypeptide (e.g., a light based, e.g., calorimetric or fluorescently detectable label, e.g., a fluorescent reporter polypeptide, e.g., GFP, EGFP, BFP, RFP); (b) evaluating the ability of a test agent to increase the activity of the reporter polypeptide in the cell, tissue or non-human animal; and (c) selecting a test agent that increases the activity of the reporter polypeptide (e.g., relative to a reference control) as an agent that increases or induces a component of the Notch signal transduction pathway. In one embodiment, the cell or tissue is a skin cell or tissue, e.g., a keratinocyte cell or tissue, e.g., a skin explant or artificial skin tissue. In another embodiment, the non-human animal is a transgenic animal, e.g., a transgenic rodent, e.g., a mouse, rat, or guinea pig, harboring the nucleic acid. In one embodiment, the component of the Notch signal transduction pathway is Notch.

In one embodiment, the method includes two evaluating steps, e.g., the method includes a first step of evaluating the test agent in a first system, e.g., a cell or tissue system, and a second step of evaluating the test agent in a second system, e.g., a second cell or tissue system or in a non-human animal. In other embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years.

In another embodiment, the effect of the agent on UVB-induced wrinkles is evaluated. For example, the agent is evaluated before, during, and/or after UVB exposure.

The agent that increases or induces the expression, activity, or levels of a component of the Notch signal transduction pathway, e.g., Notch, can be a crude or semi-purified extract, e.g., an organic, e.g., animal or botanical extract, or an isolated compound, e.g., a small molecule, protein, lipid, or nucleic acid. Typical agents are naturally occurring substances or extracts, e.g., plant or fungal extracts. For example, the agent can be any of: (a) a polypeptide component of the Notch signal transduction pathway, e.g., a Notch polypeptide or a functional fragment or mimetic thereof (e.g., the Notch intracellular domain (NICD)); (b) a peptide or protein agonist of a component of the Notch signal transduction pathway that increases an activity of the Notch signal transduction pathway, e.g., increases Notch/Notch ligand complex formation or nuclear localization of the Notch intracellular domain (NICD); (c) a small molecule that increases expression of a component of the Notch signal transduction pathway, e.g., Notch, Delta, Jagged, and RBP-Jκ, e.g., by binding to the promoter region of its gene; (d) an antibody, e.g., an antibody that binds to and stabilizes or assists the binding of a Notch pathway component to a binding partner, e.g., the binding of Notch to Jagged/Delta; (e) a chemical compound, e.g., an organic compound, e.g., a naturally occurring or synthetic organic compound that increases expression of a component of the Notch signal transduction pathway, e.g., Notch, Delta, Jagged, and RBP-Jκ; or (f) a nucleotide sequence encoding a Notch pathway polypeptide or functional fragment, analog, activated allele, or activator thereof. The nucleotide sequence can be a genomic sequence or a cDNA sequence. The nucleotide sequence can include: a Notch pathway component coding region; a promoter sequence, e.g., a promoter sequence from a Notch pathway component gene or from another gene; an enhancer sequence; untranslated regulatory sequences, e.g., a 5' untranslated region (UTR), e.g., a 5' UTR from a Notch gene or from another gene, a 3' UTR, e.g., a 3' UTR from a Notch gene or from another gene; a polyadenylation site; and/or an insulator sequence. In another embodiment, the level of a component of the Notch signal transduction pathway, e.g., Notch, Delta, Jagged, or RBP-Jκ is increased by increasing the level of expression of an endogenous component of the Notch signal transduction pathway, e.g., Notch, Delta, Jagged, or RBP-Jκ gene, e.g., by increasing transcription of the Notch gene or increasing Notch mRNA stability. In one embodiment, transcription of the Notch gene is increased by: altering the regulatory sequence of the endogenous factor Notch gene, e.g., in a somatic cell, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Notch gene to be transcribed more efficiently. In another embodiment, the agent is in a crude or partially purified botanical extract.

In one aspect, the invention features methods of reducing, treating, and/or preventing skin damage, e.g., UVB-induced skin damage and/or wrinkles, by administering to the subject an agent that increases Notch pathway activity expression or levels (e.g., a Notch pathway agonist) in an amount sufficient to reduce, treat, or prevent skin damage. In some embodiments, the agent increases or induces a component of the Notch signal transduction pathway, e.g., Notch1. In some embodiments, the methods further include identifying a subject in need of reduction, treatment, or prevention of skin damage. In some embodiments, the agent is administered topically. In some embodiments, the subject has been or will be exposed to UVB radiation. In some embodiments, the agent is selected from a PDGF receptor kinase inhibitor (e.g., AG-370 or AG-1296 (6,7-Dimethoxy-3-phenylquinoxaline)), a $K^+$ and $H^+$ ionophore (e.g., Nigericin.Na), an inhibitor of actin polymerization (e.g., Cytochalasin D), an inhibitor of sodium pumps ($Na^+/K^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). Other agonists of the Notch pathway can also be used in the methods.

In yet another aspect, the invention features methods of reducing one or more signs of skin damage, e.g., one or more of wrinkling (e.g., number or morphology of wrinkles), redness, inflammation, desquamation, and pigmentation, in a subject by administering to the subject an agent that increases Notch pathway activity, levels, or expression, in an amount sufficient to reduce wrinkles, e.g., wrinkles caused by exposure to UVB radiation. In some embodiments, the agent increases or induces a component of the Notch signal transduction pathway, e.g., Notch1. In some embodiments, the agent is selected from a PDGF receptor kinase inhibitor (e.g., AG-370 or AG-1296 (6,7-Dimethoxy-3-phenylquinoxaline)), a $K^+$ and $H^+$ ionophore (e.g., Nigericin.Na), an inhibitor of actin polymerization (e.g., Cytochalasin D), an inhibitor of sodium pumps ($Na^+/K^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). In some embodiments, the agent is administered topically. The agent can be in a composition, e.g., cosmetic composition. The composition can be sterile and/or it can further include a cosmetic agent.

In another aspect, the invention features methods of protecting against skin damage, e.g., UVB-induced skin damage in a subject by supplying to a subject a composition that includes an agent that increases Notch pathway activity, expression or levels in an amount sufficient to protect against skin damage. In some embodiments, the composition increases or induces a component of the Notch signal transduction pathway. In some embodiments, the methods further include supplying to the subject instructions for using the composition to protect against skin damage, e.g., UVB-induced skin damage and/or wrinkles. In some embodiments, the instructions include directions to apply the composition to the skin prior to, during, or after sun exposure. The composition can include a Notch pathway agonist, e.g., an agent selected from a PDGF receptor kinase inhibitor (e.g., AG-370 or AG-1296 (6,7-Dimethoxy-3-phenylquinoxaline)), a $K^+$ and $H^+$ ionophore (e.g., Nigericin.Na), an inhibitor of actin polymerization (e.g., Cytochalasin D), an inhibitor of sodium pumps (Na$^+$/K$^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). The composition can include a cosmetic agent.

The term "Notch pathway" refers to the biological components that mediate Notch signaling. The pathway includes, e.g., Notch polypeptide itself, Notch receptor, and cytoplasmic components that are modulated by receptor activation, including STAT3 and STAT5, kinases, and/or transcription factors. The term "Notch pathway agonist" refers to an agent that increases activity of the Notch pathway, e.g., an agent that potentiates, induces, or otherwise enhances one or more biological activities of a Notch receptor polypeptide, e.g., a biological activity as described herein. For example, an agonist interacts with, e.g., binds to, a Notch receptor polypeptide.

In one embodiment, the Notch pathway agonist is a Notch ligand (Notch ligand or a fragment thereof) or an amino acid sequence that is at least 85, 90, 92, 94, 95, 96, 97, 98, or 99% identical to the sequence of a Notch ligand, e.g., a Delta or Jagged polypeptide.

In another embodiment, the Notch pathway agonist is an agent that interacts with the Notch receptor. An agent that interacts with the Notch receptor can activate the receptor or otherwise agonize pathway signaling. For example, the Notch pathway agonist is a protein that interacts with the Notch receptor. The protein can comprise an agonistic anti-Notch receptor antibody (e.g., a full length antibody or an antigen-binding fragment) that interacts with and activates the Notch receptor. The protein can comprise an anti-idiotype antibody that mimics a Notch ligand (e.g. Delta or Jagged).

In one embodiment, the Notch pathway agonist is an agent that modulates a cytoplasmic Notch pathway component. An agent that modulates a cytoplasmic Notch pathway component can, for example, activate a positively acting cytoplasmic pathway component or inhibit a negatively acting cytoplasmic component. Exemplary positively acting cytoplasmic components include the Notch intracellular domain (NICD) and RBP-Jκ. The agent may also be a mimic of a positively acting component, e.g., a constitutively activated form of the Notch intracellular domain.

In one embodiment, the Notch pathway agonist is a nucleic acid that encodes a Notch polypeptide, a positively acting cytoplasmic pathway component (e.g., the Notch intracellular domain (NICD) or RBP-Jκ), a protein that interacts with (e.g., binds and/or activates) the Notch receptor, and/or a protein that modulates a cytoplasmic Notch pathway component.

The subject can be mammalian, and typically is human (e.g., a female or a male, and an adult or a juvenile human subject).

The method can further include evaluating one or more signs of skin damage in the subject, e.g., before, during, or after the administering. Examples of such signs are described herein. The method can further include evaluating a Notch associated parameter in the subject, e.g., a parameter associated with level of Notch polypeptide, Notch receptor, or Notch pathway activity. The term "parameter" refers to information, including qualitative and quantitative descriptors, e.g., values, levels, measurements, and so forth. A "Notch associated parameter" refers to a parameter that describes a Notch pathway component, e.g., the presence, absence, level, expression, stability, subcellular localization, or activity of such a component, e.g., a Notch polypeptide, a Notch receptor, or other cytoplasmic component. The parameter may also describe an mRNA that encodes a Notch pathway component.

In another aspect, the invention features compositions, e.g., cosmetic compositions, that include an agent that increases Notch pathway activity, expression, or levels (e.g., an agonist of the Notch pathway). In some embodiments the agent increases or induces a component of the Notch signal transduction pathway, e.g., Notch1. The cosmetic compositions can further include a second ingredient, e.g., a cosmetic ingredient (e.g., a fragrance, moisturizer, or sunscreen). In some embodiments, the agent that increases or induces a component of the Notch signal transduction pathway is selected from a PDGF receptor kinase inhibitor (e.g., AG-370 or AG-1296 (6,7-Dimethoxy-3-phenylquinoxaline)), a K$^+$ and H$^+$ ionophore (e.g., Nigericin.Na), an inhibitor of actin polymerization (e.g., Cytochalasin D), an inhibitor of sodium pumps (Na$^+$/K$^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). In some embodiments, the agent is a component of the Notch signal transduction pathway, e.g., a Notch ligand. These compositions can be used in methods for the treatment and/or prevention of skin damage, e.g., UVB-induced skin damage and/or wrinkles.

In another aspect, the invention features compositions, e.g., compositions for topical application, that include an agent that increases Notch pathway activity, levels, or expression, in an amount sufficient to reduce skin damage, e.g., UVB-induced skin damage and/or wrinkles. In some embodiments, the agent increases or induces a component of the Notch signal transduction pathway. The agent can be, e.g., a PDGF receptor kinase inhibitor (e.g., AG-370 or AG-1296 (6,7-Dimethoxy-3-phenylquinoxaline)), a K$^+$ and H$^+$ ionophore (e.g., Nigericin.Na), an inhibitor of actin polymerization (e.g., Cytochalasin D), an inhibitor of sodium pumps (Na$^+$/K$^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). The composition can further include a cosmetic ingredient, e.g., a fragrance or sunscreen.

In another aspect, the invention features the use of an effective amount of an agent that increases Notch pathway activity, levels, or expression in the preparation of a medicament or cosmetic to preventing, reducing, and/or treating skin damage, e.g., UVB-induced skin damage and/or wrinkles. In some embodiments, the agent increases or induces a component of the Notch signal transduction pathway. The agent can be, e.g., a PDGF receptor kinase inhibitor (e.g., AG-370 or AG-1296 (6,7-Dimethoxy-3-phenylquinoxaline)), a K$^+$ and H$^+$ ionophore (e.g., Nigericin.Na), an inhibitor of actin polymerization (e.g., Cytochalasin D), an inhibitor of sodium pumps (Na$^+$/K$^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). The medicament or cosmetic can further include a cosmetic ingredient, e.g., a fragrance or sunscreen.

In yet another aspect, the invention features kits for reducing, treating, or preventing skin damage, e.g., UVB-induced skin damage and/or wrinkles, in a subject that include a composition that includes an agent that increases Notch pathway activity, levels, or expression, e.g., an agent increases or induces a component of the Notch signal transduction pathway, and instructions for using the composition to prevent skin damage. The composition can further include a cosmetic ingredient, e.g., a fragrance or sunscreen. The instructions can include directions to apply the composition to the skin prior to, during, or after sun exposure.

In another aspect, the invention features methods of treating a Notch-associated disorder in a subject by identifying a subject in need of treatment for a Notch-based disorder and administering to the subject an agent selected from a PDGF receptor kinase inhibitor (e.g., AG-370 or AG-1296 (6,7-Dimethoxy-3-phenylquinoxaline)), a $K^+$ and $H^+$ ionophore (e.g., Nigericin.Na), an inhibitor of actin polymerization (e.g., Cytochalasin D), an inhibitor of sodium pumps ($Na^+/K^+$ ATPase) (e.g., Ouabain), an inhibitor of mitochondrial oxidative phosphorylation (e.g., FCCP (carbonylcyanide-4-(trifluoromethoxy)-phenylhydrazone)), and a c-Jun N-terminal kinase (JNK) inhibitor (e.g., SP600125). In some embodiments, the Notch-based disorder is a cancer, e.g., a cancer of the skin, liver, prostate, or cervix. In some embodiments, the cancer cells are infected with a human papilloma virus.

The details of one or more embodiments of the invention are set forth in the accompanying drawings and the description below. Other features, objects, and advantages of the invention will be apparent from the description and the claims. All references cited herein are incorporated by reference.

DETAILED DESCRIPTION

Figure 1:
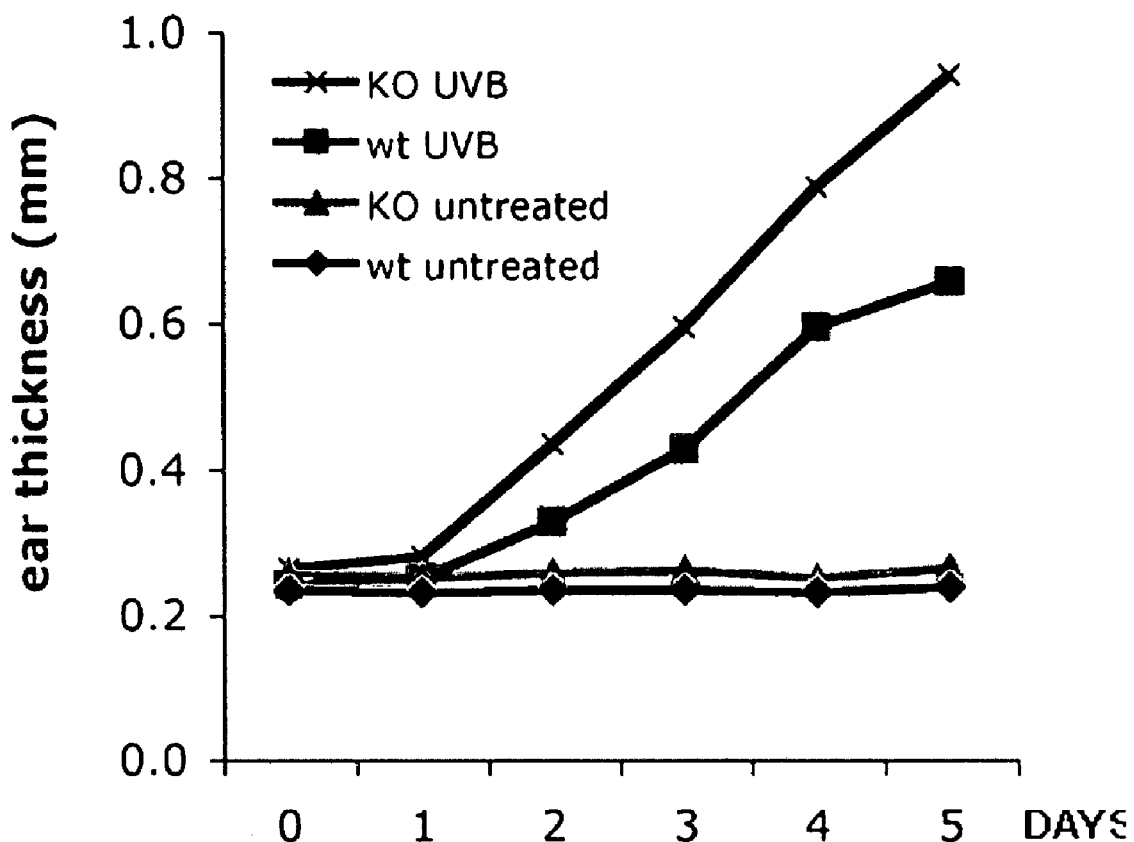
FIG. 1 is a line graph depicting thickness of UVB-irradiated mouse ears for five days following UVB treatment.

The inventors have identified the Notch signal transduction pathway as a target for screening and therapeutic methods as well as compositions, e.g., cosmetic compositions, for treatment, prevention, and/or reduction of skin damage, e.g., UVB-induced skin damage, e.g., wrinkles. This invention features compositions having a Notch inducer as an active ingredient.

Skin Damage

Damaged skin is typically characterized by one or more of inflammation, epidermal hyperplasia, dermal elastosis and matrix protein degradation, and the presence of perivenular lymphohistiocytic dermal infiltrates. Results described herein reveal that Notch protects against skin damage, e.g., skin damage caused by UVB radiation.

An effective amount of a composition is defined as the amount of the composition which, upon administration to a subject, prevents or reduces one or more signs of skin damage, e.g., inflammation, epidermal hyperplasia, dermal elastosis and matrix protein degradation, perivenular lymphohistiocytic dermal infiltrates, and the formation of wrinkles (e.g., fine wrinkles), in the subject. The effective amount to be administered to a subject is typically based on a variety of factors including age, sex, surface area, weight, and conditions of the skin. Body surface area may be approximately determined from height and weight of the patient. See, e.g., *Scientific Tables*, Geigy Pharmaceuticals, Ardley, N.Y., 1970, 537. Effective doses will vary, as recognized by those skilled in the art, dependent on route of administration, excipient usage, and the possibility of co-usage with other treatments such as usage of other wrinkle reducing compounds. An experimental animal can be used in a method of determining an effective amount of a composition.

As used herein, "preventing or treating skin damage" means the application or administration of a therapeutic agent to a subject who has skin damage, e.g., a wrinkle, or has a predisposition toward skin damage, or has been exposed to an agent likely to cause skin damage, e.g., UV radiation, e.g., UVB radiation, with the purpose to reduce, improve, alleviate, alter, remedy, ameliorate, or affect the appearance of skin damage. The therapeutic agent can be administered to the subject by the subject himself or herself, or by another person, e.g., a health care provider or a provider of cosmetics. In preferred embodiments of the methods described herein, skin damage is reduced in the subject by at least 5%, typically at least 10%, e.g., at least 20%, 25% or more.

The methods and compositions can be used prophylactically or they can be used to reduce, treat, and/or prevent further skin damage, e.g., wrinkles, or reduce the appearance of skin damage in a subject. The composition can also be used for the manufacture of a medicament or cosmetic for preventing, reducing, and/or treating skin damage, e.g., wrinkles.

Wrinkles

Wrinkles are generally a result of the natural aging process of the skin and of exposure to the sun's ultraviolet rays. A wrinkle is a configuration change in the surface of the skin, without specific structural alterations at the histological level. Generally, wrinkles are classified as described in Kligman et al. (1985) *Br. J. Derm.* 113:37-42, incorporated herein by reference. Kligman classifies wrinkles into three classes: linear wrinkles, glyphic wrinkles, and crinkles. Linear wrinkles are straight, found generally in the facial skin, and are caused by natural aging or exposure to ultraviolet light. Glyphic wrinkles are shaped as apparent triangles or rectangles of wrinkles, are found on the face, hands, and neck exposed to sunlight, and are aggravated by exposure to ultraviolet light or dermatoheliosis. Crinkles are thin, crinkled wrinkles on flabby skin, found anywhere on the skin, but typically on the backs of hands and around the eyelids.

Linear wrinkles can be further subclassified into (a) regular wrinkles and (b) fine wrinkles. Regular wrinkles are long, deep, clear, and are also referred to as crow's feet. Fine wrinkles are thin and shallow. Regular wrinkles have a width of at least about 155 microns (0-32 Hz), typically about 160 to 250 microns. Fine wrinkles have a width of less than about 154 microns, typically about 40 to 154 microns (32-126 Hz), as calculated, e.g., in a power spectrum obtained through transforming three dimensional shape data into data in a frequency domain by two-dimensional Fourier transformation (using, e.g., the Shiseido Wrinkle Analyzer 3D Pro system, essentially as described in Takasu et al. (1996) *J. Soc. Cosmet. Chem. Japan* 29:394-405; and Japanese Published Patent Application No. 07-113623, published May 2, 1995).

Methods of Screening

The Notch signal transduction pathway, including Notch, Delta, Jagged, and RBP-Jκ/CBF-1, is well characterized (see, e.g., Artavanis-Tsakonas et al. (1999) *Science* 284:770-776 and Okuyama et al. (2004) *J. Investig. Dermatol. Symp. Proc.* 9:248-252). The components of the pathway have been cloned, and their protein and gene sequences are readily available to one of ordinary skill in the art. For example, cloning of a human Notch cDNA and gene was described in Ellison et al. (1991) *Cell* 66:649-61; GenBank Accession No. $NM_{13}$ 017617. Reporter constructs of Notch pathway activity have been described, e.g., in Jarriault et al. (1995) *Nature* 377:355-8; Maier and Gessler (2000) *Biochem. Biophys. Res. Commun.* 225:652-60; Rangarajan et al. (2001) *EMBO J.* 20:3427-36; Itoh et al. (2004) *EMBO J.* 23:541-551; and Okuyama et al. (2004) *Developmental Cell* 6:551-62. Notch controlled promoters typically contain at least one conserved motif for RBP-Jκ/CBF-1 binding, typically GGCGCC (SEQ ID NO:1) GTGGGAA (SEQ ID NO:2) and/or CAGC, or variants thereof.

A compound that increases Notch pathway activity is any compound, e.g., a small molecule, protein, peptide, or antibody, that increases the expression of a Notch-controlled promoter. A Notch-controlled promoter is a promoter that is induced by the Notch intracellular domain (NICD). Exemplary Notch-controlled promoters include promoters of Hes-1, Hey-2 (Herp2), caspase 3, and p21. Increasing the expression of a Notch-controlled promoter can be accomplished by any means, including increasing the expression, levels, or activity of a positive regulator of the Notch pathway, e.g., upstream or downstream of Notch; and decreasing the expression, levels, or activity of a negative regulator of the Notch pathway, e.g., upstream or downstream of Notch.

Numerous methods exist for evaluating whether an agent alters the expression, levels, or activity of a particular mRNA or protein. In one embodiment, the ability of a test agent to modulate (e.g., increase or decrease) (e.g., permanently or temporarily) expression from a Notch-controlled promoter is evaluated by, e.g., reporter (e.g., luciferase, LacZ, or GFP) transcription assay. For example, a cell or transgenic animal, the genome of which comprises a reporter gene operably linked to a Notch-controlled promoter, can be contacted with a test agent, and the ability of the test agent to increase or decrease reporter activity is indicative of the ability of the agent to modulate Notch. In another embodiment, the ability of a test agent to modulate Notch expression, levels, or activity is evaluated in a transgenic animal. The effect of a test agent on Notch expression, levels, or activity may be evaluated on a cell, cell lysate, or subject, typically a non-human experimental mammal, e.g., a rodent (e.g., a rat, mouse, rabbit), or explant (e.g., skin) thereof. Numerous methods of assessing Notch mRNA expression are well know in the art, e.g., Northern analysis, ribonuclease protection assay, reverse transcription-polymerase chain reaction (RT-PCR) or RNA in situ hybridization (see, e.g., Sambrook et al. *Molecular Cloning: A Laboratory Manual* ($3^{rd}$ ed. 2001)). The levels of Notch protein may be monitored by, e.g., Western analysis, immunoassay, or in situ hybridization. Notch activity (e.g., altered promoter binding and/or transcription activity) may be determined by, e.g., electrophoretic mobility shift assay, DNA footprinting or reporter gene assay. Typically, the effect of a test agent on Notch expression, levels, or activity is evaluated in a transgenic cell or non-human animal, or explant or cell derived therefrom. General methods of small-molecule screening are discussed in, e.g., Schrieber (2003) *Chem. & Eng. News* 81:51-61; and Flaumenhaft and Sim (2003) *Chem. Biol.* 10:481-6.

Agents

Agents to be tested in the screening methods described herein include crude or purified extracts of organic sources, e.g., animal or botanical extracts, as well as partially or fully purified or synthetic agents, e.g., small molecules, polypeptides, lipids and/or nucleic acids, ad libraries of these. Agents that are identified as inducers of Notch can be tested and/or used in the skin damage-related methods and compositions described herein.

Several agents that induce Notch are identified herein, including PDGF receptor kinase inhibitors (e.g., AG-370 and AG-1296 (6,7-Dimethoxy-3-phenylquinoxaline)), $K^+$ and $H^+$ ionophores (e.g., Nigericin.Na), inhibitors of actin polymerization (e.g., Cytochalasin D), inhibitors of sodium pumps ($Na^+/K^+$ ATPase) (e.g., Ouabain), inhibitors of mitochondrial oxidative phosphorylation (e.g., FCCP (carbonyl-cyanide-4-(trifluoromethoxy)-phenylhydrazone)), and c-Jun N-terminal kinase (JNK) inhibitors (e.g., SP600125). These and structurally or functionally similar agents can be tested and/or used in the treatment of Notch-associated disorders, e.g., skin damage, wrinkles, and cancers, e.g., cancers of the skin, liver, cervix, and prostate, and cancers that are caused by a human papilloma virus (see, e.g., Talora et al. (2002) *Genes Dev.* 16:2252-2263; Nicolas et al. (2003) *Nature Genet.* 33:416-421; Qi et al. (2003) *Cancer Res.* 63:8323-9). Other Notch-inducing agents are described in Liu et al. (2003) *Mol. Cell. Biol.* 23:14-25 and US 2006/0128619. Further, some virally encoded proteins can modulate the activity of the Notch pathway (see, e.g., Hayward (2004) *Semin. Cancer Biol.* 14:387-396 and Hayward et al. (2006) *Sci. STKE* 2006: re4). Viral activators of the Notch pathway can be directly administered to a subject or administered as nucleic acids encoding the viral activators.

In one aspect, Notch pathway agonists are used to reduce, treat, and/or prevent, or ameliorate skin damage. Exemplary Notch pathway agonists include a Notch polypeptide, a Notch intracellular domain, Notch ligands, e.g., Delta/Jagged, agents that activate or agonize Notch receptor, and agents that modulate other Notch pathway components to activate Notch pathway signaling. Exemplary agonists bind to Notch receptor with high affinity, e.g., with an affinity constant of less than about $10^7 M^{-1}$, about $10^8 M^{-1}$, or, about $10^9 M^{-1}$ to $10^{10} M^{-1}$ or stronger.

In one embodiment, a Notch pathway agonist is an agent that interacts with Notch receptor, but is other than a Notch ligand. For example, the agent can be an immunoglobulin, e.g., a full length antibody or antibody fragment, that interacts with a Notch receptor and that activates Notch pathway signaling activity, e.g., by agonizing the receptor. The antibody can be an anti-idiotype antibody designed to mimic binding of a Notch ligand.

In one embodiment, a Notch pathway agonist is an agent (e.g., an immunoglobulin) that stabilizes a Notch/ligand interaction, e.g., by binding one or both of Delta/Jagged and Notch receptor.

In one embodiment, a Notch pathway agonist is a molecule that leads to the production of more Notch intracellular domain (NICD) or more NICD targeted to the nucleus (see, e.g., Kau and Silver (2003) *Drug Discov. Today* 8:78-85; Kau et al. (2004) *Nature Reviews Cancer* 4:1-12). The distribution of NICD in the cell can be monitored by automated microscopy (Mitchison (2005) *Chembiochem* 6:33-39).

Antibodies

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FRs and CDRs has been precisely defined (see, e.g., Kabat, E. A., et al. (1991) *Sequences of Proteins of Immunological Interest, Fifth Edition*, US Department of Health and Human Services, NIH Publication No. 91-3242; and Chothia, C. et al. (1987) *J. Mol. Biol.* 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulfide bond (see, e.g., A. F. Williams and A. N. Barclay (1988) *Ann. Rev Immunol.* 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site").

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibodies can be generated by a variety of means, including immunization, e.g., using an animal, or in vitro methods such as phage display. All or part of an antigen can be used as an immunogen or as a target for selection. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Accordingly, by using hybridoma technology, at least partly human, antigen-specific monoclonal antibodies with the desired specificity can be produced and selected. See, e.g., XENOMOUSE™, Green et al. (1994) *Nat. Gen.* 7:13-21; US 2003-0070185; U.S. Pat. No. 5,789,650; and WO 96/34096.

Non-human antibodies can also be produced, e.g., in a rodent. The non-human antibody can be humanized, e.g., as described in EP 239 400; US Pat. Nos. 6,602,503; 5,693,761; and 6,407,213, deimmunized, or otherwise modified to make it effectively human.

Fully human monoclonal antibodies can be produced, e.g., using in vitro-primed human splenocytes, as described by Boemer et al. (1991) *J. Immunol.* 147:86-95. They may be prepared by repertoire cloning as described by Persson et al. (1991) *Proc. Nat. Acad. Sci. USA* 88:2432-2436 or by Huang and Stollar (1991) *J. Immunol. Methods* 141:227-236; also U.S. Pat. No. 5,798,230. Large nonimmunized human phage display libraries may also be used to isolate high affinity antibodies that can be developed as human therapeutics using standard phage technology (see, e.g., Hoogenboom et al. (1998) *Immunotechnology* 4:1-20; Hoogenboom et al. (2000) *Immunol Today* 2:371-378; and US 2003-0232333).

Antibodies and other proteins described herein can be produced in prokaryotic and eukaryotic cells. In one embodiment, the antibodies (e.g., scFv's) are expressed in a yeast cell such as Pichia (see, e.g., Powers et al. (2001) *J. Immunol. Methods* 251:123-35), Hanseula, or Saccharomyces.

Antibodies, particularly full length antibodies, e.g., IgGs, can be produced in mammalian cells. Exemplary mammalian host cells for recombinant expression include Chinese Hamster Ovary (CHO cells) (including dihydrofolate reductase-negative CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell can be a mammary epithelial cell.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

Administration

The pharmaceutical compositions for the prevention or reduction of wrinkles or other skin conditions, or for the treatment of other disorders described herein, may be administered via the parenteral route, including topically, subcutaneously, intraperitoneally, intramuscularly, intranasally, and intravenously. Topical administration is typically used. Repeated administration of the composition, e.g., repeated topical administration, can be used. More than one route of administration can be used simultaneously, e.g., topical administration in association with oral administration. Examples of parenteral dosage forms include aqueous solutions of the active agent in a isotonic saline, 5% glucose, or other well-known pharmaceutically acceptable excipient. Solubilizing agents, such as cyclodextrins or other solubilizing agents, can be utilized as pharmaceutical excipients for delivery of the wrinkle reducing composition.

A composition described herein can also be formulated into dosage forms for other routes of administration utilizing conventional methods. A pharmaceutical composition can be formulated, for example, in dosage forms for oral administration in a capsule, a tablet (each including timed release and sustained release formulations), or a gel seal. Capsules may comprise any standard pharmaceutically acceptable material such as gelatin or cellulose derivatives. Tablets may be formulated in accordance with the conventional procedure by compressing mixtures of an agent and a solid carrier, and a lubricant. Examples of solid carriers include starch and sugar bentonite. A pharmaceutical composition can also be administered in a form of a hard shell tablet or capsule containing, for example, lactose or mannitol as a binder and a conventional filler and a tableting agent.

Topical administration of the compounds, e.g., wrinkle-reducing compounds, described herein presents a preferred route of administration amongst the many different routes described above. For topical application, the composition can include a medium compatible with skin. Such topical pharmaceutical compositions can exist in many forms, e.g., in the form of a solution, cream, ointment, gel, lotion, shampoo, or aerosol formulation adapted for application to the skin. The weight percent of the active ingredient in the composition useful in preventing or reducing wrinkles or in the treatment of a disorder described herein typically ranges from 0.01% to 10% (e.g., 0.02%, 0.05%, 0.1%, 0.2%, 0.5%, 1.0%, 2.0%, 5.0%, or 10%) (based on the total weight of the composition) in admixture with a pharmaceutically acceptable carrier. A wide variety of carrier materials can be employed in the wrinkle reducing composition described herein such as alcohols, aloe vera gel, allantoin, glycerine, vitamin A and E oils, mineral oils, and polyethylene glycols. Other additives, e.g., preservatives, fragrance, sunscreen, or other cosmetic ingredients, can be present in the composition. The topical composition can be applied and removed immediately, or it can be applied and left on the skin surface, e.g., the face, for an extended period of time, e.g., overnight or throughout the day.

UVB Radiation

The major source of UVB radiation is natural sunlight. The intensity of UVB rays varies depending on the time of day, time of year, the sun's position in the sky, altitude and distance from the equator. These rays are most intense during the midday hours in the summer, although they are always present, even during the winter months. Distance above sea level and distance from the equator are also important to consider. The higher the altitude the greater the intensity of UVB rays. Therefore, mountaineers, skiers, and those who live at high altitudes are at risk of long term UVB damage. Also, the nearer one is to the equator the more intense the UV radiation and the higher the risk of long term UVB damage.

Snow, water, and sand reflect sunlight, magnifying the amount of UVB radiation that reaches the skin. Even when clouds obscure the sun, UVB levels can still be sufficiently high to cause skin damage, e.g., wrinkles, upon long term exposure.

The UV index (developed by the Environmental Protection Agency) indicates the intensity of the sun's UV rays on a given day. There are four categories—moderate (UV index is less than 3), high (UV index is 3 to 6) very high (UV index is 6 to 10) and extreme (UV index is greater than 10). A moderate UV Index means it will take more than an hour to burn your skin; an extreme level means it will take less than 15 minutes. The index is often included with weather reports. Clinically, UVB exposure is measured in MEDs. One MED is the amount of UVB required to produce a sunburn in sensitive skin. Because the effects of UVB exposure are cumulative, long term or chronic UVB induced wrinkles can occur as a result of long term exposure to UVB levels below those which, upon acute exposure, can cause erythema or edema or burning (e.g., below one MED). For example, a subject is at risk of long term UVB induced wrinkles if the subject is chronically exposed to the sun even if the subject is only exposed to the sun during days with a low or moderate UV Index.

Measurement of Wrinkles

The effect of a compound on the formation or appearance of wrinkles can be evaluated qualitatively, e.g., by visual inspection, or quantitatively, e.g., by computer assisted measurements of wrinkle morphology. Preferably, wrinkle morphology is quantitatively analyzed. Examples of quantitative methods for measuring wrinkles include, but are not limited to, the optical cut technique employing a laser beam, as proposed by Hoshino (1992) *Pixel* 45:121, herein incorporated by reference; or methods that analyze three-dimensional skin replicas, e.g., the Shiseido Wrinkle Analyzer 3D Pro system (Takasu et al. (1996) *J. Soc. Cosmet. Chem. Japan* 29:394-405; Japanese Published Patent Application No. 07-113623, published May 2, 1995 (corresponds to U.S. patent application Ser. No. 08/364,346)). The SILFLO® (Flexico Development Ltd., Potters Bar, UK) system or a similar system can be used to take a replica of the skin. Irregularities on the surface of the skin replica, i.e., wrinkles, are analyzed, e.g., with the Shiseido Wrinkle Analyzer 3D Pro or a similar system, to provide three-dimensional shape data from the heights at points on a two-dimensional plane corresponding to the skin. According to the three-dimensional data, the length, width, depth, area, and volume of each wrinkle is calculated. According to the parameters for regular and fine wrinkles described herein, different classes of wrinkles, including the subclasses of regular and fine wrinkles, can thus be individually recognized and scored.

Kits

An agent that increases Notch pathway activity, e.g., an agent identified through a method described herein, e.g., AG-370, AG-1296 (6,7-Dimethoxy-3-phenylquinoxaline), Nigericin.Na, Cytochalasin D, Ouabain, FCCP (carbonylcyanide-4-(trifluoromethoxy)-phenylhydrazone), or SP600125, can be provided in a kit. The kit includes (a) the agent, e.g., a composition that includes the agent, and (b) informational material. The informational material can be descriptive, instructional, marketing, or other material that relates to the methods described herein and/or the use of the agent for the methods described herein. For example, the informational material relates to wrinkles or their prevention or reduction.

In one embodiment, the informational material can include instructions to administer the agent in a suitable manner to perform the methods described herein, e.g., in a suitable dose, dosage form, or mode of administration (e.g., a dose, dosage form, or mode of administration described herein). A preferred dose, dosage form, or mode of administration is topical, e.g., on the skin. In another embodiment, the informational material can include instructions to administer the agent to a suitable subject, e.g., a human, e.g., a human having, or at risk for, wrinkles. For example, the material can include instructions to administer the agent to the face, neck or hands.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, electronic mail address, web address, or telephone number, where a user of the kit can obtain substantive information about the agent and/or its use in the methods described herein. Of course, the informational material can also be provided in any combination of formats.

In addition to the agent, the composition of the kit can include other ingredients, such as a solvent or buffer, a stabilizer, a preservative, a fragrance or other cosmetic ingredient, and/or a second agent for treating a condition or disorder described herein, e.g., a sunscreen. Alternatively, the other ingredients can be included in the kit, but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution is typically an aqueous solution, e.g., a sterile aqueous solution. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers, or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent. For example, the kit includes a plurality of syringes, ampules, foil packets, or blister packs, each containing a single unit dose of the agent. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

The following specific examples are to be construed as merely illustrative, and not limiting of the remainder of the disclosure in any way whatsoever.

EXAMPLES

Example 1

Notch1 Protects Against Inflammation by UVB Irradiation

Mice with a keratinocyte-specific deletion of the Notch1 gene (Notch1$^{-/-}$ mice) are described in Rangarajan et al. (2001) *EMBO J.* 20:3427-36. Female Notch1$^{-/-}$ mice (Notch1 ko) and Notch$^{+/+}$ littermate controls (wild type) (8 weeks of age, n=2 per group) were tested for ear swelling responses following UVB irradiation. Ear thickness was measured using a thickness gauge (Mitsutoyo Corp.) prior to irradiation, and each day for three days following UVB irradiation (80 and 160 mJ/cm$^2$). The results are presented in Table 1 (80 mJ/cm$^2$ UVB) and Table 2 (160 mj/cm$^2$).

TABLE 1

Increase of ear thickness after 80 mJ/cm$^2$ irradiation

|  | day 0 | 1 | 2 | 3 |
|---|---|---|---|---|
| Notch1 ko | 100.0% | 100.0 | 103.4 | 141.4 |
| wild type | 100.0% | 100.0 | 100.0 | 100.0 |

TABLE 2

Increase of ear thickness after 160 mJ/cm$^2$ irradiation

|  | day 0 | 1 | 2 | 3 |
|---|---|---|---|---|
| Notch1 ko | 100.0% | 103.0 | 124.6 | 178.7 |
| wild type | 100.0% | 100.0 | 120.4 | 148.2 |

More swelling was observed after UVB irradiation in Notch1 knock out mice, as compared with wild type mice.

In a similar experiment, 12-week old Notch1 ko and wild-type control littermate mice were exposed to 500 mJ/cm$^2$ UVB on the right ear, while the left ear was left untreated and used as an internal control. Treatment was given on day 0, and ear thickness was measured for 5 days following UVB irradiation (FIG. 1). Increased swelling in response to UVB was observed in the Notch1 knock out mouse.

These results indicate that Notch1 is protective against UVB-induced swelling and inflammation.

Example 2

Notch1 Protects Against Skin Damage by UVB Irradiation

Female Notch1$^{-/-}$ mice and Notch$^{+/+}$ littermate controls (8 weeks of age, n=1 per group) were clipped of hair, then used in UVB irradiation experiments to measure skin damage (80, 160, and 240 mJ/cm$^2$). Two mice were used as non-irradiated controls. Back skin samples were obtained from mice (control mice and UVB irradiated mice at 24, 48, and 72 hours after UVB irradiation) and hematoxylin and eosin (HE) staining was performed on 7 μm sections. Representative sections were obtained from mice and evaluated using an Olympus BH-2 microscope (Olympus). Skin damage was evaluated with five categories (−: no damage; ±: slight damage; +: clear damage; ++: strong damage, +++: severe damage). The results are presented in Table 3.

TABLE 3

Skin damage after UVB irradiation

|  |  |  | UVB | | |
| --- | --- | --- | --- | --- | --- |
|  |  | no UVB | day 1 | 2 | 3 |
| Notch1 ko | no UVB | — | | | |
|  | 80 mJ/cm$^2$ (1 MED) |  | n.d. | +~++ | + |
|  | 160 mJ/cm$^2$ (2 MED) |  | + | +~++ | ++ |
|  | 240 mJ/cm$^2$ (3 MED) |  | n.d. | ++ | ++ |
| wild type | no UVB | — | | | |
|  | 80 mJ/cm$^2$ (1 MED) |  | n.d. | + | + |
|  | 160 mJ/cm$^2$ (2 MED) |  | + | ± | + |
|  | 240 mJ/cm$^2$ (3 MED) |  | n.d. | + | ++ | n.d.: not determined

More skin damage was observed in Notch1 ko mice following UVB irradiation, as compared with wild type UVB irradiated mice. Histological analysis showed accumulation of inflammatory cells in the upper dermis and elastic tissues and fibers in the dermis in Notch1 knock out mice, as compared with wild mice. These results indicate that Notch 1 protects against skin damage caused by UVB radiation.

Example 3

Notch1 Knock Out Mice Show Increased Wrinkle Formation

Female Notch1$^{-/-}$ mice and Notch$^{+/+}$ littermate controls (10 weeks of age, n=2 per group) were clipped of hair, then subjected to UVB irradiation for 10 weeks. Long term UVB irradiation (cumulative UVB dose: 6.8 J/cm$^2$) produced pronounced wrinkle formation in Notch1 deficient mice, as compared with wild type mice. Wrinkling was evaluated with five categories (0: no wrinkling; 1: slight wrinkling; 2: clear wrinkling; 3: strong wrinkling; 4: severe wrinkling).

TABLE 4

Wrinkling after long term UVB irradiation

|  | mouse number | | |
| --- | --- | --- | --- |
|  | 1 | 2 | average |
| Notch1 ko | 3 | 2 | 2.5 |
| wild type | 1 | 1 | 1 |
| Notch1 ko (no UVB) | 0 | 0 | 0 |
| wild type (no UVB) | 0 | 0 | 0 |

More wrinkling was observed in Notch1 knock out mice, as compared with wild and non-irradiated mice. Histological analysis showed accumulation of inflammatory cells in the upper dermis and elastic tissues in the dermis in Notch1 knock out mice, as compared with wild type and non-irradiated mice.

Example 4

Identification of Activators of Notch Signaling in Keratinocytes by High Throughput Screening of Chemical Libraries in a Cell Based Assay The results of a high throughput screen of a variety of chemical compounds for Notch activators are presented. The pHTS-RBP-luciferase reporter plasmid, which contains 12 RBP-Jκ-binding repeats (GTGGGAA; SEQ ID NO:2) from the EBV TP1 promoter (Laux et al. (1994) *J. Virol.* 68:6947-6958) in front of the TATA box, was used to screen for Notch activators. The reporter was transiently transfected in 293 E/T cells prior to plating of the cells in 384 well plates. The chemical compounds were then pin-transferred into the plates in nanoliter volumes using a robotic tool. The screens were done as part of the ICCB (Institute of Chemistry and Cell Biology)-Longwood Investigator Initiated Screening Program.

The library used in these initial experiments was the BIOMOL ICCB Known Bioactives library. This collection was purchased from BIOMOL (Plymouth Meeting, Pa.; catalogue #2840; www.biomol.com) and plated. The collection includes many classes of compounds, including ion channel blockers, G-protein coupled receptor ligands, second messenger modulators, nuclear receptor ligands, actin and tubulin ligands, kinase inhibitors, protease inhibitors, gene regulation agents, lipid biosynthesis inhibitors, as well as other well-characterized compounds that perturb cell pathways.

Molecules that induced the Notch-response reporter over 2-fold were considered positive hits. These molecules, which are identified as potential positive regulators of the Notch pathway in cells, are listed in Table 5.

TABLE 5

Positive regulators of the Notch pathway

| Compound | Molecular Weight | Description | References |
| --- | --- | --- | --- |
| AG-370 | 259 | AG-370 is a member of the tyrphostin family of tyrosine kinase inhibitors and is a selective inhibitor of the PDGF receptor | Levitzki and Gilon, 1991, *Trends Pharmacol. Sci.* 12: 171-4; Bryckaert et al., 1992, *Exp. Cell Res.* 199: 255-61 |

TABLE 5-continued

Positive regulators of the Notch pathway

| Compound | Molecular Weight | Description | References |
|---|---|---|---|
| | | kinase ($IC_{50}$ = 20 µM) versus the EGF receptor kinase. AG-370 inhibits PDGF-induced mitogenesis in human bone marrow fibroblasts. | |
| AG-1296 (6,7-Dimethoxy-3-phenylquinoxaline) | 266 | A potent inhibitor of PDGF receptor tyrosine kinase ($IC_{50}$ = 1 µM). Also inhibits FGF tyrosine kinase and c-kit. Induces apoptosis in a small-cell lung cancer cell line (H526). | Kovalenko et al., 1997, *Biochemistry* 36: 6260-9; Strutz et al., 2001, *Kidney Int.* 59: 579-92; Krystal et al., 1997, *Cancer Res.* 57: 2203-8 |
| Nigericin•Na | 747 | $K^+$ and $H^+$ ionophore. stimulates $Ca^{2+}$ release from mitochondrial stores by disruption of membrane potential. Induces rapid intracellular acidification, resulting in apoptosis. | Vercesi et al., 1993, *J. Biol. Chem.* 268: 8564-8; Furlong et al., 1997, *J. Cell Sci.* 110: 653-61 |
| Cytochalasin D | 507.6 | Cytochalasin D is a cell permeable fungal toxin which binds to the barbed end of actin filaments inhibiting both the association and dissociation of subunits. It causes the disruption of actin filaments and inhibition of actin polymerization. | Cooper, 1987, *J. Cell Biol.* 105: 1473-8; Flanagan and Lin, 1980, *J. Biol. Chem.* 255: 835-8; Goddette and Frieden, 1986, *J. Biol. Chem.* 261: 15974-80; Schliwa, 1982, *J. Cell Biol.* 92: 79-91 |
| Ouabain | 728.8 | Ouabain is a steroidal inhibitor of cardiac sodium pumps ($Na^+/K^+$ATPase) which has recently been recognized as an endogenous adrenal hormone. In the CNS it can be used as a tool to induce in vivo excitotoxicity. Ouabain, as well as other endogenous digitalis-like compounds, can downregulate the expression of 14-3-3 proteins in rat lens. | McDonnough et al., 2002, *Basic Res. Cardiol.* 97: I19-24; Schoner, 2002, *Eur. J. Biochem.* 269: 2440-8; Veldhuis et al., 2003, *J. Neurosci.* 23: 4127-33; Lichtstein et al., 2000, *Hypertens. Res.* 23: S51-3 |
| FCCP Carbonylcyanide-4-(trifluoromethoxy)-phenylhydrazone | 254.2 | A potent reversible inhibitor of mitochondrial oxidative phosphorylation. FCCP is a useful tool for depolarizing mitochondrial membrane potential. Treatment of cells with FCCP at varying concentrations leads to partial (100 nm) or complete (10 µM) depolarization and apoptosis. | Collins et al., 2000, *Biochem. J.* 347: 593-600; Keij et al., 2000, *Cytometry* 39: 203-10; Gautier et al., 2000, *Neuroreport* 11: 2953-6 |
| SP600125 | 220.2 | A novel potent and selective JNK-1, -2, -3 inhibitor ($IC_{50}$ = 0.11 µM). SP600125 is a reversible ATP competitive inhibitor with >20-fold selectivity versus a range of kinases. It dose-dependently inhibits the phosphorylation of c-jun and the expression of inflammatory genes COX-2, IL-2, IFN-gamma, and TNF-alpha. In vivo, it | Bennett et al., 2001, *Proc. Natl. Acad. Sci. USA* 98: 13681-6; Han et al., 2001, *J. Clin. Invest.* 108: 73-81 |

TABLE 5-continued

Positive regulators of the Notch pathway

| Compound | Molecular Weight | Description | References |
|---|---|---|---|
| | | blocks LPS-induced expression of TNF-alpha and inhibits anti CD3-induced apoptosis of CD4+ CD8+ thymocytes. | |

In conclusion, a high throughput genetic approach was developed to identify and study positive regulators of Notch signaling. The identification of small molecule candidates for the targeted activation of the Notch pathway is reported. These molecules, listed in Table 5, can be used as Notch-inducing agents to treat and/or prevent Notch-related disorders in subjects, e.g., cancer or skin damage, or as lead compounds for further screening to identify agents for use in treating and/or preventing Notch-related disorders.

Example 5

Figure 2A:
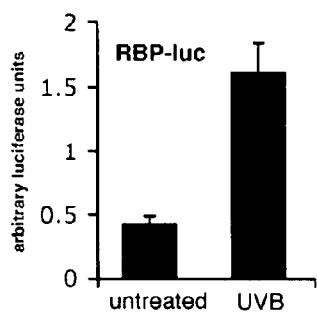
FIG. 2A is a chart depicting luciferase activity of a RBP-luc reporter in mouse primary keratinocytes exposed to UVB.
Figure 2B:
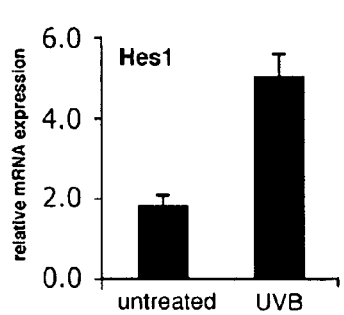
FIG. 2B is a chart depicting relative mRNA expression of Hes-1, as compared to GADPH, in mouse primary keratinocytes exposed to UVB.

UVB Exposure Activates Notch Signaling and Notch is Protective Against UVB-Induced Apoptosis The induction of endogenous Notch activity by UVB was measured in primary mouse keratinocytes. Primary keratinocytes were transiently transfected with a Notch-responsive reporter plasmid (RBP-luc). Luciferase activity was measured 24 hours after UVB treatment (100 mJ/cm$^2$). Activity of the RBP-luc reporter was more than 3-fold higher in the UVB-treated cells than in the control, untreated cells (FIG. 2A). Induction of Notch activity was also examined by assaying endogenous expression of a "canonical" Notch responsive gene, Hes-1, in primary keratinocytes. Primary keratinocytes were exposed to 50 mJ/cm$^2$ UVB treatment, and mRNA was collected 24 hours later from treated and control cells. The mRNAs were analyzed by real-time RT-PCR, using GAPDH levels for normalization. Hes-1 expression was 2-3 fold higher in the UVB treated cells than in the control cells (FIG. 2B). The induction of Hes-1 expression following UVB treatment was time-dependent. Similar results were observed for Hey-2.

Figure 2C:
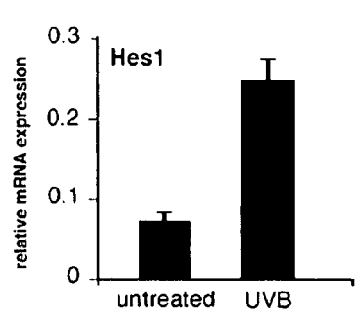
FIGS. 2C and 2D are charts depicting relative mRNA expression of Hes-1 and Keratin 1, as compared to GADPH, in mouse skin exposed to UVB.
Figure 2D:
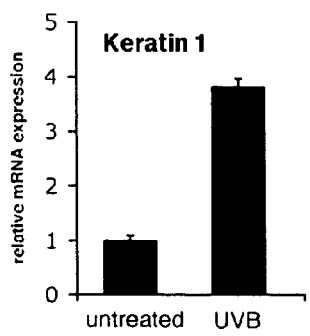

The induction of endogenous Notch activity by UVB was also measured in vivo. Mice were treated for four hours with 220 mJ/cm$^2$ UVB. mRNAs from heat-separated epidermis were analyzed by real time RT-PCR using GAPDH levels for normalization. The canonical Notch response gene, Hes1 (FIG. 2C), and a Notch-inducible keratinocyte differentiation marker, Keratin 1 (FIG. 2D), were expressed 3-4 fold higher in UVB treated skin than in control skin.

Figure 2E:
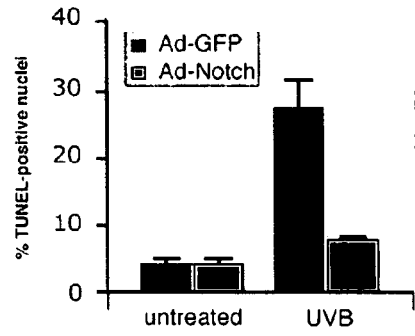
FIG. 2E is a chart depicting the percentage of TUNEL-positive nuclei (indicating apoptosis) in mouse primary keratinocytes infected with adenovirus expressing activated Notch or GFP control exposed to UVB.
Figure 2F:
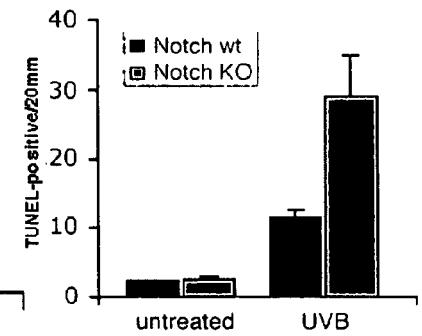
FIG. 2F is a chart depicting the number of TUNEL-positive keratinocytes per 20 $mm^2$ of Notch wt and Notch knock out mouse skin following UVB irradiation.

Notch was also found to be protective against apoptosis in response to UVB treatment in vitro and in vivo. Primary mouse keratinocytes were infected with a recombinant adenovirus expressing a constitutively active form of Notch1 or a GFP control. Sixteen hours after infection, the cells were UVB irradiated (50 mJ/cm$^2$), and the apoptotic response was evaluated 8 hours later by TUNEL assay. Apoptosis in response to UVB was reduced about 3-fold in the cells expressing constitutively activated Notch1 compared to the GFP control (FIG. 2E). Similarly, deletion of the Notch1 gene increased the susceptibility of keratinocytes to UVB induced apoptosis in vivo. Mice with an induced deletion of Notch1 in the epidermis and wild type littermate controls were exposed to UVB (160 mJ/cm$^2$) and apoptosis was assessed by TUNEL assay 48 hours later. In each case two mice were analyzed, and the fraction of TUNEL positive keratinocytes was determined by counting a minimum of 300 cells over three independent fields. UVB-induced apoptosis was 2-3 fold higher in keratinocytes deleted in Notch1 (FIG. 2F).

Example 6

Notch Signaling is Protective Against Apoptosis Induced by DNA Damage

Figure 3A:
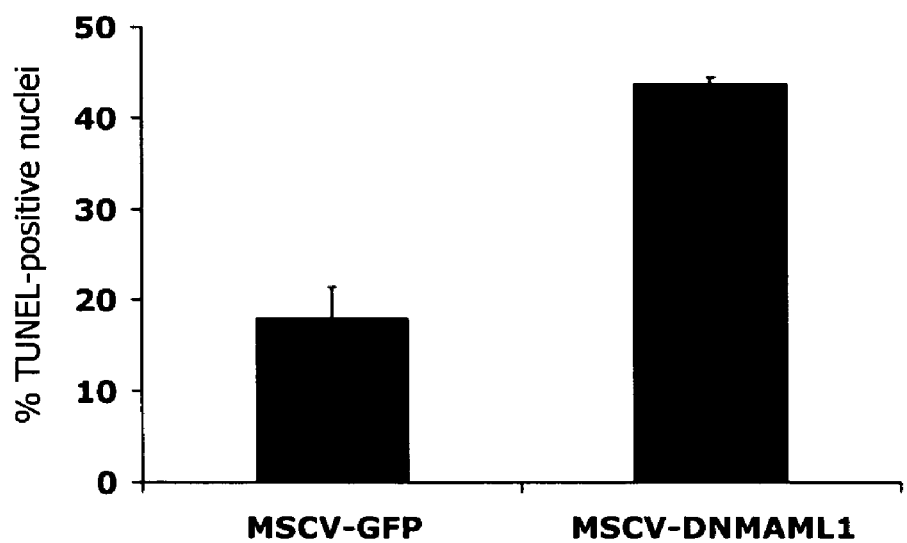
FIG. 3A is a chart depicting the percentage of TUNEL-positive nuclei (indicating apoptosis) in mouse primary keratinocytes infected with mouse stem cell virus (MSCV) expressing the Notch signaling inhibitor MAM51 (MSCV-DNMAML1) or a GFP control (MSCV-GFP) following treatment with 4-nitroquinoline 1-oxide (4-NQO).
Figure 3B:
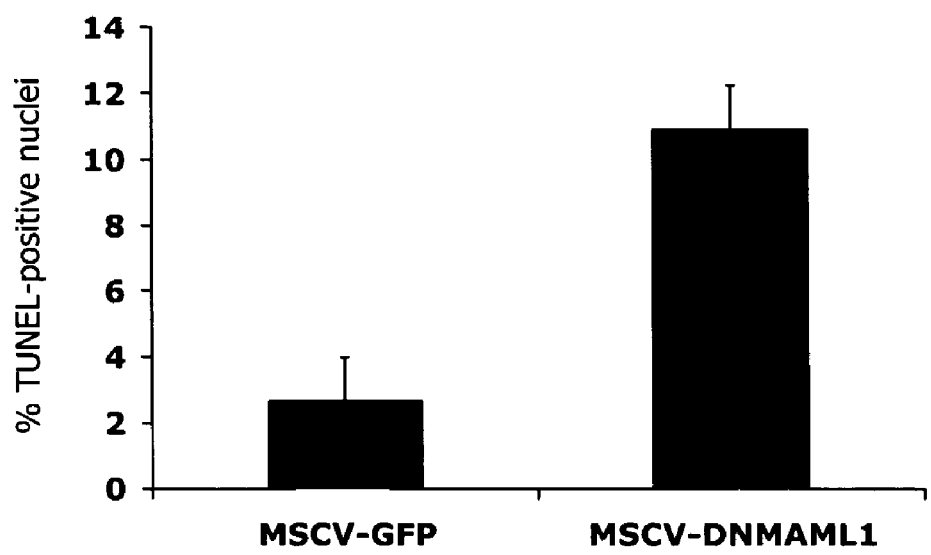
FIG. 3B is a chart depicting the percentage of TUNEL-positive nuclei (indicating apoptosis) in mouse primary keratinocytes infected with mouse stem cell virus (MSCV) expressing the Notch signaling inhibitor MAM51 (MSCV-DNMAML1) or a GFP control (MSCV-GFP) following UVB irradiation.

To demonstrate that Notch signaling plays a protective function against DNA-damage induced apoptosis, we measured apoptosis by TUNEL assay in DNA-damaged primary human keratinocytes infected with a retroviral vector expressing a 51 amino acid peptide of the MAML1 protein (MAM51), as a specific tool to suppress Notch/CBF-1-dependent transcription (Weng et al. (2003) *Mol. Cell Biol.* 23:655-664). Keratinocytes were treated with 2 μM 4-nitroquinoline 1-oxide (4-NQO) or 300 mJ/cm$^2$ UVB, and apoptosis was assayed 12 hours later. A significantly higher apoptotic response (2-5 fold) was observed in MAM51-expressing keratinocytes (FIGS. 3A-B), indicating that Notch1 protected against apoptosis induced by these DNA damaging agents.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating skin damage caused by ultraviolet radiation in a subject, the method comprising:
   identifying a subject in need of treatment for skin damage caused by ultraviolet radiation; and
   administering to the subject a composition comprising an agent that increases Notch pathway activity for the purpose of treating the identified skin damage, wherein the agent is selected from the group consisting of: AG-370, AG-1296 (6,7-dimethoxy-3-phenylquinoxaline), nigericin•Na, cytochalasin D, FCCP (carbonylcyanide-4-(trifluoromethoxy)-phenylhydrazone), and SP600125, thereby treating the skin damage in the subject.

2. The method of claim 1, wherein the composition is administered topically.

3. The method of claim 1, wherein the Notch is Notch1.

4. The method of claim 1, wherein the skin damage is caused by UVB radiation.

5. The method of claim 1, wherein the skin damage is wrinkles.

6. The method of claim 1, wherein the agent is AG-370.

7. The method of claim 1, wherein the agent is AG-1296.

8. The method of claim 1, wherein the agent is nigericin.Na.

9. The method of claim 1, wherein the agent is SP600125.

10. A method of protecting against skin damage caused by ultraviolet radiation in a subject, the method comprising:
    identifying a subject in need of reduction of skin damage caused by ultraviolet radiation; and
    administering to the subject a composition comprising an agent that increases Notch pathway activity for the purpose of reducing skin damage in the subject, wherein the agent is selected from the group consisting of: AG-370, AG-1296 (6,7-dimethoxy-3-phenylquinoxaline), cytochalasin D, FCCP (carbonylcyanide-4-(trifluoromethoxy)-phenylhydrazone), and SP600125.

11. The method of claim 10, wherein the agent is administered topically.

12. The method of claim 10, wherein the Notch is Notch1.

13. The method of claim 10, wherein the skin damage is caused by UVB radiation.

14. The method of claim 10, wherein the skin damage is wrinkles.

15. The method of claim 10, wherein the agent is AG-370.

16. The method of claim 10, wherein the agent is AG-1296.

17. The method of claim 10, wherein the agent is SP600125.

18. The method of claim 1, wherein the agent is cytochalasin D.

19. The method of claim 1, wherein the agent is FCCP.

20. The method of claim 10, wherein the agent is cytochalasin D.

21. The method of claim 10, wherein the agent is FCCP.

* * * * *

UNITED STATES PATENT AND TRADEMARK OFFICE
CERTIFICATE OF CORRECTION

PATENT NO.         : 8,114,422 B2
APPLICATION NO.    : 11/497870
DATED              : February 14, 2012
INVENTOR(S)        : Seishiro Fujii et al.

It is certified that error appears in the above-identified patent and that said Letters Patent is hereby corrected as shown below:

Title page, col. 2, line 7, Abstract, delete "sin" and insert -- skin --

Col. 23, lines 43-44, claim 8, delete "nigericin.Na." and insert -- nigericin•Na --

Signed and Sealed this
Twenty-seventh Day of November, 2012

David J. Kappos
*Director of the United States Patent and Trademark Office*